United States Patent
Charan et al.

(10) Patent No.: US 8,546,573 B2
(45) Date of Patent: Oct. 1, 2013

(54) PROCESS FOR THE PREPARATION OF 7-ETHYL-10-[4-(1-PIPERIDINO)-1-PIPERDINO] CARBONYLOXY-CAMPTOTHECIN HYDROCHLORIDE TRIHYDRATE

(75) Inventors: Ganpat Dan Shimbhu Charan, Gujarat (IN); Arun Ankush Tanpure, Gujarat (IN); Kumar Kamlesh Laxmi Singh, Gujarat (IN)

(73) Assignee: Cadila Healthcare Limited, Ahmedabad (IN)

( * ) Notice: Subject to any disclaimer, the term of this patent is extended or adjusted under 35 U.S.C. 154(b) by 169 days.

(21) Appl. No.: 12/943,601

(22) Filed: Nov. 10, 2010

(65) Prior Publication Data

US 2011/0144342 A1 Jun. 16, 2011

(30) Foreign Application Priority Data

Nov. 18, 2009 (IN) .......................... 2665/MUM/2009

(51) Int. Cl.
*C07D 471/22* (2006.01)
(52) U.S. Cl.
USPC .......................................................... 546/48
(58) Field of Classification Search
USPC .......................................................... 546/48
See application file for complete search history.

(56) References Cited

U.S. PATENT DOCUMENTS 4,721,771 A * 1/1988 Jansons et al. ................. 528/222
7,662,964 B2 * 2/2010 Laitinen ........................ 546/189

FOREIGN PATENT DOCUMENTS

WO WO2006016203 * 2/2006

OTHER PUBLICATIONS

Seddon "Pseudopolymorph . . ." Crystal. growth $ design v.4(6) 1047 (2004).*
Wikipeid "Solvents" p. 1-10 (2012).*
"Properties of solvents" p. 1-7 (2012).*
Kirk-Othmer Encyclopedia of Chem. Tech. "Crystallization" p. 95-147 (2002).*
Sawada et al. "Synthesis and . . . " Chem. Pharm. Bull. 39(6) 1446-1454 (1991).*
Jinan Boss Chemical Industry Co. "1-Chlorocarbonyl-4-piperidinopiperidine " p. 1 (2012).*
Hohance Chemical Co. "1-Chlorocarbonyl-4-piperidinopiperidine" p. 1 (2012).*

* cited by examiner

*Primary Examiner* — Celia Chang
(74) *Attorney, Agent, or Firm* — Ladas & Parry LLP (57) ABSTRACT

The present invention relates to process for the preparation of 7-ethyl-10-[4-(1-piperidino)-1-piperidino]carbonyloxy-camptothecin hydrochloride trihydrate and process for the isolation of 1-chlorocarbonyl-4-piperidinopiperidine and novel crystalline form of 1-chlorocarbonyl-4-piperidinopiperidine and 7-ethyl-10-[4-(1-piperidino)-1-piperidino]carbonyloxy-camptothecin.

8 Claims, 4 Drawing Sheets

PROCESS FOR THE PREPARATION OF 7-ETHYL-10-[4-(1-PIPERIDINO)-1-PIPERDINO] CARBONYLOXY-CAMPTOTHECIN HYDROCHLORIDE TRIHYDRATE

FIELD OF INVENTION

The present invention discloses improved processes for preparing 7-ethyl-10-[4-(1-piperidino)-1-piperidino]carbonyloxy-camptothecin hydrochloride trihydrate and a process for the isolation of 1-chlorocarbonyl-4-piperidinopiperidine, one of the intermediates in the preparation of 7-ethyl-10-[4-(1-piperidino)-1-piperidino]carbonyloxy-camptothecin. Also provided is new impurity of CPT-11 and process for preparation thereof.

BACKGROUND OF THE INVENTION 7-ethyl-10-[4-(1-piperidino)-1-piperidino]carbonyloxy-camptothecin is known as Irinotecan and has the structure represented in Formula (I). The drug is available in the hydrochloride trihydrate form of 7-ethyl-10-[4-(1-piperidino)-1-piperidino]carbonyloxy-camptothecin herein after referred to as CPT-11.

Formula I 7-ethyl-10-[4-(1-piperidino)-1-piperidino]carbonyloxy-camptothecin is a camptothecin derivative that is highly active against lung and colorectal cancer and has been used for treating several types of tumors. It is sold in the form of the hydrochloride trihydrate salt (CPT-11) under the trade name CAMPTOSAR.

CPT-11 has shown activity against a variety of tumor types, particularly refractory colorectal tumors, and is used for the treatment of various forms of cancer. Its primary use is in the treatment of colon cancer, particularly advanced colon cancer. It is also of interest for treatment of other cancers, such as cancers of the lung, the stomach and the pancreas.

The compound of formula (I) was first disclosed in U.S. Pat. No. 4,604,463 which, describes a broad family of camptothecin derivatives including formula (I), its pharmaceutically acceptable salts and preparation thereof. The same patent also describes a process for the preparation of compound of formula (I) comprising condensation of 7-ethyl-10-hydroxy camptothecin with 1-chlorocarbonyl-4-piperidinopiperidine in presence of pyridine at room temperature.

Compound of formula (I) is usually prepared semi synthetically from natural camptothecin, which occurs in a Chinese tree, *Camptotheca acuminata*. Sawada et al., Chem. Pharm. Bull. Vol. 39, No. 6, 1446-54 (1991), describes the preparation of compound of formula (I) and crystal structure of its hydrochloride trihydrate (also known as CPT-11) that is currently used for the manufacturing of the commercially available product). Crystalline form of CPT-11 as described by Sawada et al. is herein after referred to, for convenience, as "Form b". It is also characterized by PXRD peaks at about 7.60, 8.30, 9.55, 11.0 and 12.40°±0.2 degrees 2θ.

In the reference cited above, the method of preparation of the compound formula (I) from natural camptothecin involves five chemical steps and subsequently the base is converted to the HCl salt. This method suffered from very low yield (20%). Hence, there is a need in the art to develop a simple and efficient process for the bulk production of compound of formula (I).

WO2006084941 discloses process for the preparation of compound of formula (I) and its pharmaceutically acceptable salts. This process involves elimination of [1,4']-bipiperidinyl-1'-carbonyl chloride by adding suitable amine after completion of the reaction.

Polymorphism, the occurrence of different solid-state forms, is a property of many molecules and molecular complexes. A single molecular entity may give rise to a variety of solid state forms having distinct crystal structures and physical properties such as melting point, powder X-ray diffraction pattern, infrared (IR) absorption fingerprint and different physicochemical properties. One solid-state form may give rise to several polymorphic forms, which are different from one another in all the above properties.

WO2003074527 disclosed a polymorphic form of crystalline hydrochloride salt of formula (I) characterized by PXRD peaks at about 9.15, 10.00, 11.80, 12.20, 13.00 and 13.4°+0.2 degrees 2θ.

WO2007035709 disclosed four polymorphic forms of crystalline hydrochloride salt of formula (I) characterized by powder X-ray diffraction peak value as depicted in below Table 1.

TABLE 1

| Form I | Form II | Form III | Form IV |
| --- | --- | --- | --- |
| 12.34 | 20.39 | 23.96 | 9.19 |
| 24.79 | 22.29 | 20.92 | 9.98 |
| 10.94 | 12.07 | 21.08 | 18.89 |
| 8.20 | 8.48 | 21.09 | 15.27 |
| 27.67 | 11.83 | 23.83 | 16.16 |
| 22.72 | 15.75 | 24.32 | 25.74 |
| 21.23 | 18.52 | 10.28 | 27.06 |

WO2008148260 disclosed a polymorphic form of crystalline hydrochloride salt of formula (I) characterized by PXRD peaks at about 7.80, 9.96, 13.28, 15.62, 19.98, 20.36, 22.34, 22.66 and 30.18°±0.2 degrees 2θ.

Though several processes for preparing both the compound formula (I) as well as its hydrochloride salt are known, only few are environmental friendly and economically viable processes for the preparation of highly pure CPT-11. Further, in most of the prior art references, the [1,4']-bipiperidinyl-1'-carbonyl chloride (II) has been stated to be unstable and therefore the preparation of compound of formula (I) is normally carried out through the formation of the HCl salt of (II). We have surprisingly found that [1,4']-bipiperidinyl-1'-carbonyl chloride prepared according to the process of the present invention is stable and can be isolated. We herein therefore disclose the stable form of [1,4']-bipiperidinyl-1'-carbonyl chloride (II). The use of the stable form reduces the formation of the impurities and also substantially increases the yield of the final compound (I).

We herein disclose improved process for the preparation of the compound of formula (I) and also process for the preparation of the hydrochloride salt of compound formula (I) prepared according to the process of the present invention.

The process being environmental friendly and economically viable, for the preparation of highly pure CPT-11. We herein also disclose a new impurity of CPT-11, process of preparation of these impurities, which may be used as reference standards.

In order to obtain marketing approval for a new drug product, manufacturers must submit to the regulatory authority evidence that the product is acceptable for administration to humans. Such a submission must include impurity profile of the product to demonstrate that the impurities are either absent, or present in a negligible amount. Different regulatory authorities have promulgated guidelines requiring applicants to identify the impurities present in the product and also disclose their concentration in the product. They also provide the maximum level of impurities allowable in the product. Thus for e.g. USFDA recommends that drug applicants identify all the impurities having concentration of 0.1% or greater in the active ingredient. Therefore, there is a need to check impurity profile and identify the impurities and also their concentration in the active ingredient.

The product mixture of a reaction rarely is a single compound pure enough to comply with pharmaceutical standards. Side products and byproducts of the reaction and adjunct reagents used in the reaction will, in most cases, be present. At certain stages during processing of the CPT-11 contained in the product mixture into an active pharmaceutical ingredient, it must be analyzed for purity, typically by HPLC or GC analysis.

Generally, impurities (side products, byproducts and adjunct reagents) are identified spectroscopically and by other physical methods and then the impurities are associated with a peak position in a chromatogram. Thereafter, the impurity can be identified by its position in the chromatogram, which is conventionally measured in minutes between injection of the sample on the column and elution of the particular component through the detector, known as "retention time". This time period varies daily based upon the condition of the instrumentation and many other factors. To mitigate the effect that such variations have upon accurate identification of an impurity, practitioners use "relative retention time" (RRT) to identify impurities. The RRT of an impurity is its retention time divided by the retention time of some reference marker. Thus, it is sometimes desirable to select an alternative compound that is added to, or is present in, the mixture in an amount significant enough to be detectable and sufficiently low as not to saturate the column and to use that as the reference marker. Researchers and developers in drug manufacturing understand that a compound in a relatively pure state can be used as a reference standard" (a "reference marker is similar to a reference standard but it is used for qualitative analysis) to quantify the amount of the compound in an unknown mixture. When the compound is used as an "external standard" a solution of a known concentration of the compound is analyzed by the same technique as the unknown mixture.

The reference standard compound also can be used to quantify the amount of another compound in mixture if the "response factor", which compensates for differences in the sensitivity of the detector to the two compounds, has been predetermined.

The reference standard compound can even be used as an internal standard when the unknown mixture contains some of the reference standard compound by using a technique called "standard addition" wherein at least two samples are prepared by adding known and differing amounts of the internal standard. The proportion of detector response due to the reference standard compound that is originally in the mixture can be determined by extrapolation of a plot of detector response versus the amount of the reference standard compound that was added to each of the sample to zero.

OBJECTIVES OF THE INVENTION

The main objective of the present invention is to provide an improved process for the preparation of CPT-11 of formula (I).

The present invention also provides a method for the preparation of impurity free compound of formula (I), achieved by coupling of the [1,4']-bipiperidinyl-1'-carbonyl chloride (II) with 7-ethyl-10-hydroxy camptothecin (III) in the presence of suitable amide and using suitable solvents.

In an embodiment of the invention, compound of the formula (I) is crystallized from suitable crystallization solvents.

Figure 2:
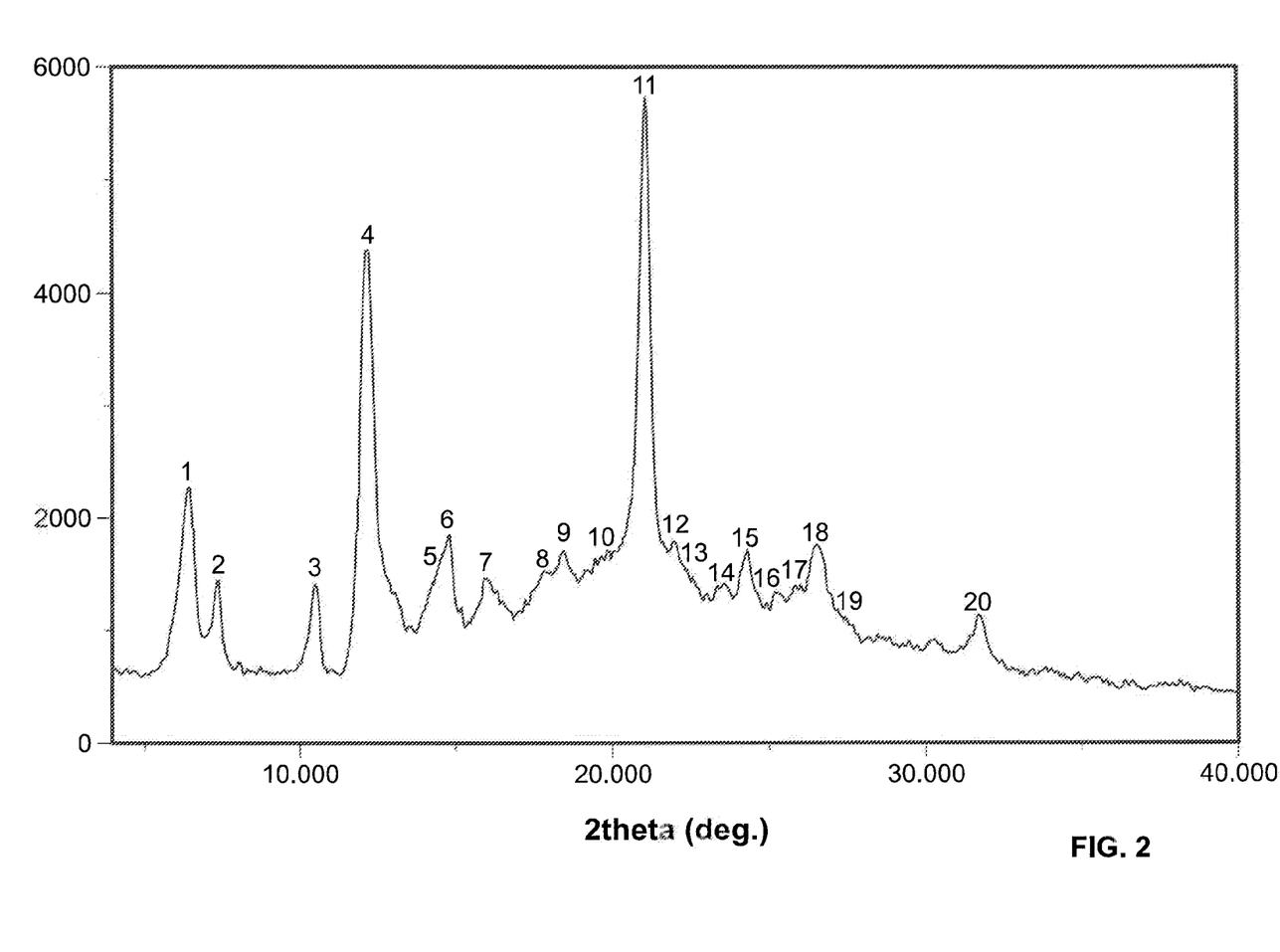
FIG. 2 is a powder X-ray diffraction (XRPD) pattern of the crystalline form of compound of formula (I) of the present invention.

In another embodiment, the invention also discloses crystalline form of compound of formula (I), characterized by a PXRD pattern substantially as depicted in FIG. 2.

Figure 1:
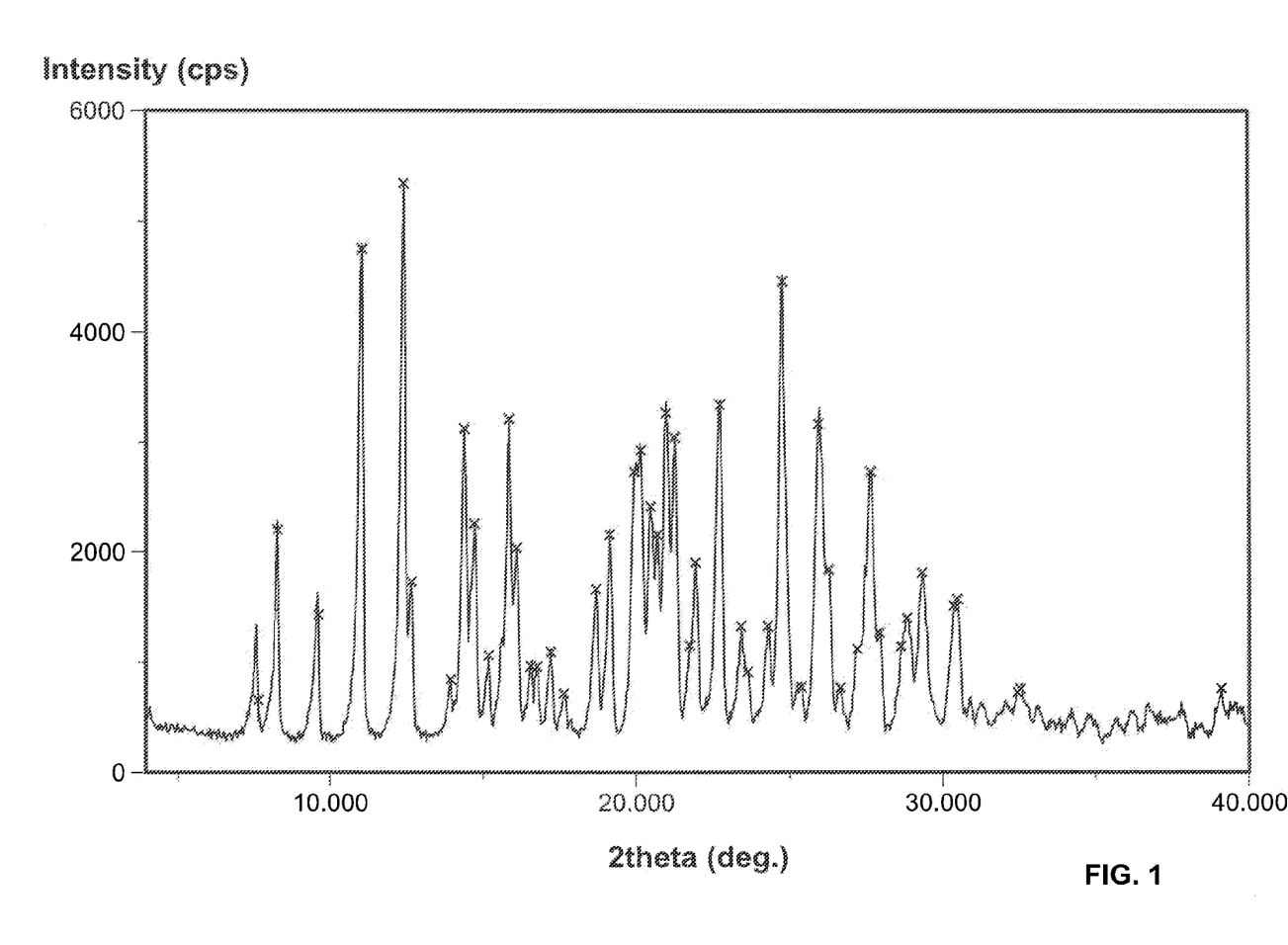
FIG. 1 is a powder X-ray diffraction (XRPD) pattern of the crystalline CPT-11 according to the present invention.

In another embodiment, the invention also discloses crystalline form of CPT-11, characterized by a PXRD pattern substantially as depicted in FIG. 1.

In a still further embodiment is provided a process for isolation of [1,4']-bipiperidinyl-1'-carbonyl chloride.

In a further embodiment is provided [1,4']-bipiperidinyl-1'-carbonyl chloride as a stable solid form.

Figure 3:
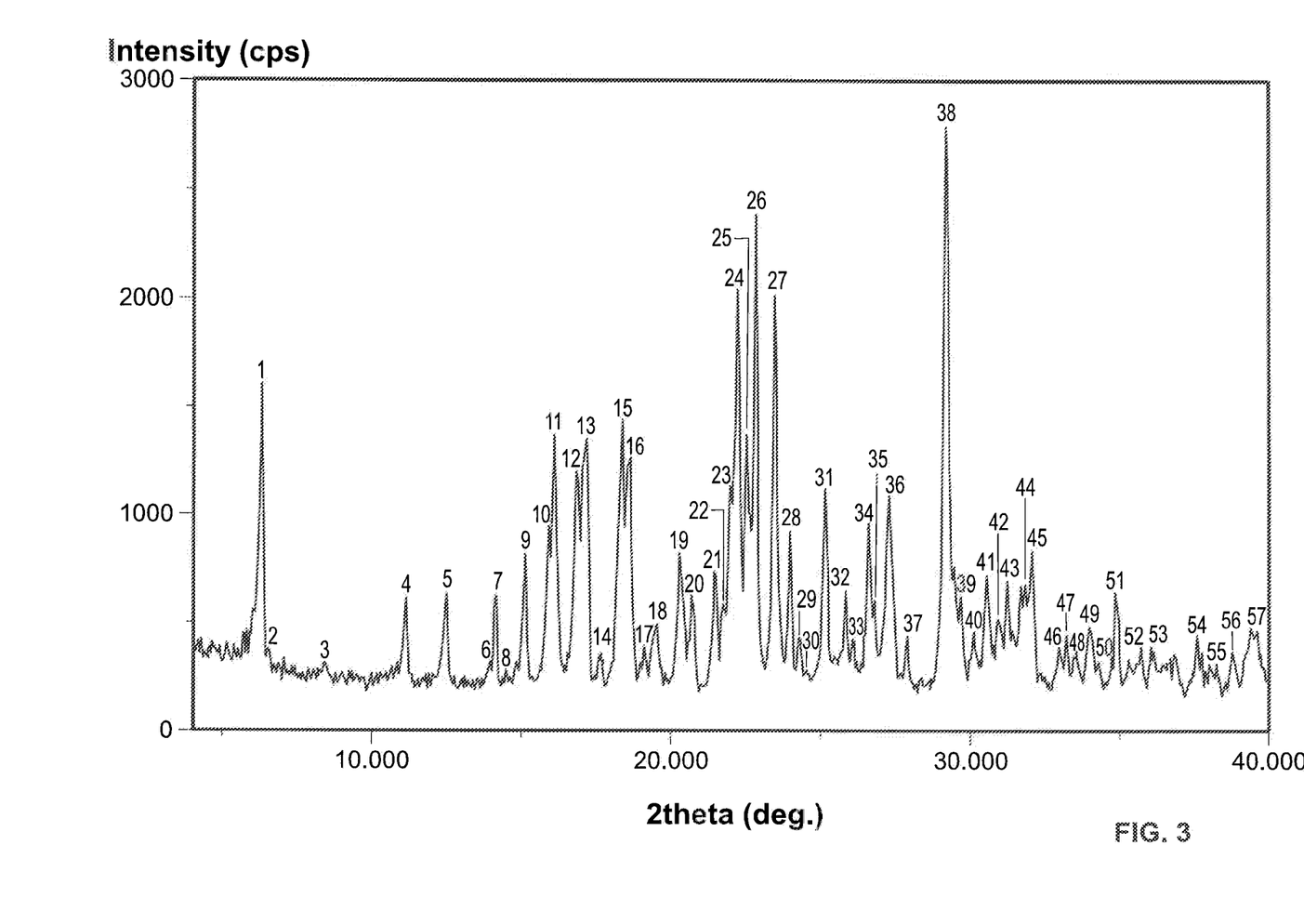
FIG. 3 is a powder X-ray diffraction (XRPD) pattern of the crystalline [1,4']bipiperidinyl-1'-carbonyl chloride (II) according to the present invention.
Figure 4:
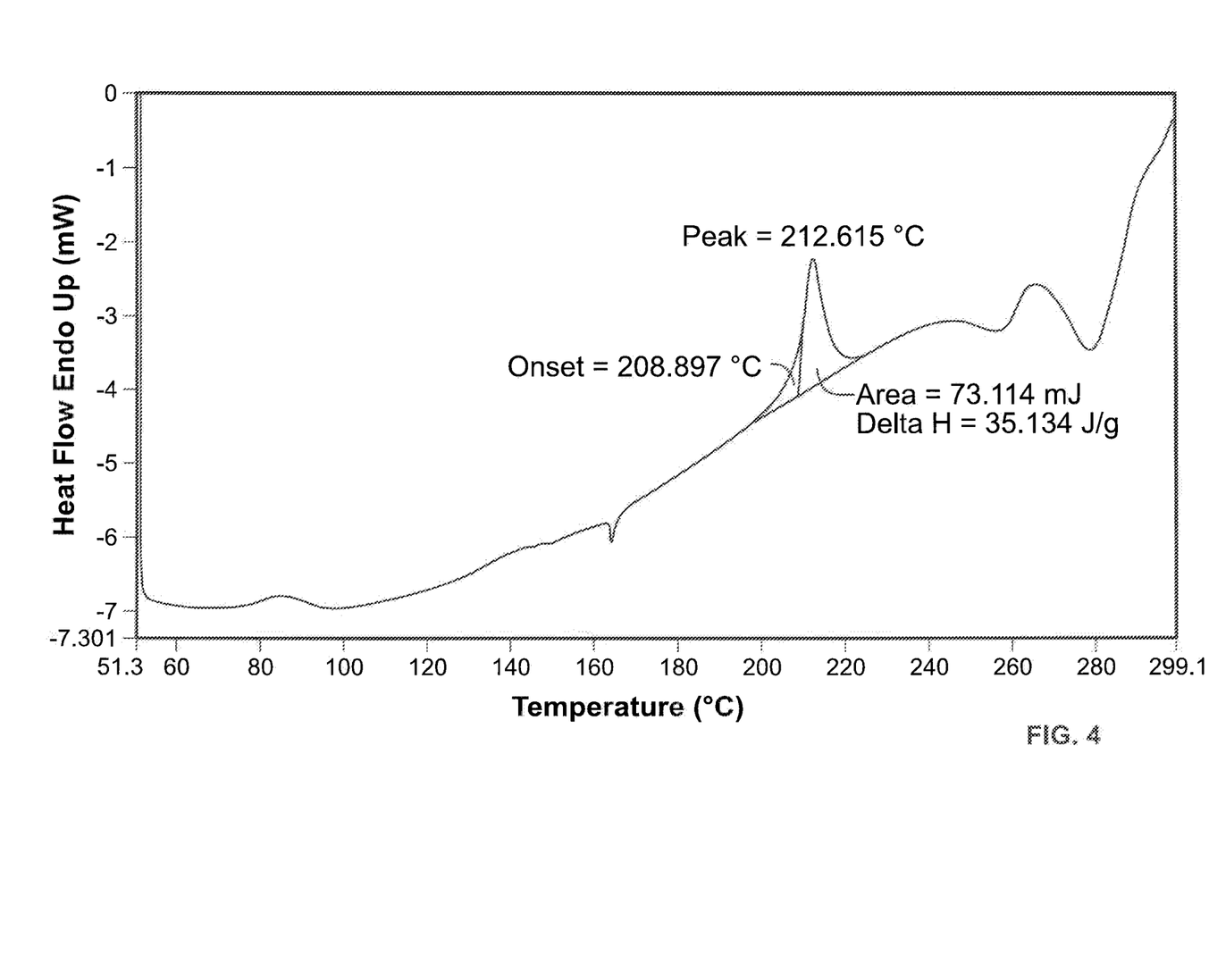
FIG. 4 is a differential scanning calorimetric curve of the crystalline [1,4']bipiperidinyl-1'-carbonyl chloride (II) according to the present invention.

In a still further embodiment is provided a crystalline form of [1,4']-bipiperidinyl-1'-carbonyl chloride characterized by a PXRD pattern substantially as depicted in FIG. 3.

The present invention also discloses a novel compound (S)-4,11-diethyl-3,14-dioxo-3,4,12,14-tetrahydro-1H-pyrano[3',4':6,7]indolizino[1,2-b]quinoline-4,9-diyl bis([1,4'-bipiperidine]-1'-carboxylate) of formula (X), as an impurity and process for preparation thereof.

The above and other embodiments are further described in the following paragraphs.

DETAILED DESCRIPTION

As used herein, the term "reflux temperature" refers to the boiling point of the solvent.

As used herein, the term "PXRD" refers to powder X-ray diffraction.

As used herein, the term "TEA" refers to triethyl amine. As used herein, the term "DMSO" refers to dimethyl sulfoxide, as used herein, the term "DMAC" refers to dimethyl acetamide, as used herein, the term "NMP" refers to N-methylpyrrolidone, as used herein, the term SN-38 refers to formula (III).

As used herein, the term "7-ethyl-10-[4-(1-piperidino)-1-piperidino]carbonyloxy-camptothecin hydrochloride trihydrate" refers to CPT-11.

i) The complete x-ray powder spectrum, which was recorded with a Rigaku 2.0 Kilowatt X-ray powder diffractometer model using copper radiation. The X-ray diffraction pattern was recorded by keeping the instrument parameters listed below:
X-ray: Cu/40 kv/30 mA, Diverging slit: 1°, Scattering slit: 1°, Receiving slit: 0.15 mm, Monochromator RS: 0.8 mm, Counter: Scintillation counters; Scan mode: Continuous, Scan speed: $4.000^{deg.}$/min., Sampling width: 0.010°, Scan axes: 2θ vs CPS, Scan range: 4° to 40.0°, Theta offset: 0.000.
ii) Differential scanning calorimetric analysis was carried out in a DSC-60 model from Shimadzu (S/W: TA-60WS Acquisition version 2.1.0.0) by keeping following parameters: Sample Size Approx. 1-2 mg, Sample Pans: Hermetic/Crimping Pans, Start Temperature: 50° C., End Temperature: 300° C., Rate of Heating: 10° C./min., Purge Gas: Nitrogen, Flow-rate: 20 ml/min

The present invention provides improved processes for the preparation of CPT-11 as outlined in Scheme-1.

quantity of the reactant prevents the formation of any dimer impurity at this step, which is a problem reported in earlier processes. In the present invention we discloses the process for the preparation of compound of formula (II) in which high molar ration of triphosgene is used as compare to the substrate. High molar ration is selected from 1.4 to 3.5 equivalent as phosgene of substrate preferably 1.4 to 2.2 moles equivalent as phosgene of substrate. In an embodiment, the addition is carried out over 2-3 hours followed by stirring for an hour Further, in most of the prior art references, the [1,4']-bipiperidinyl-1'-carbonyl chloride (II) has been stated to be unstable and therefore the preparation of compound of formula (I) is normally carried out through the formation of the HCl salt of (II). We have surprisingly found that [1,4']-bipiperidinyl-1'-carbonyl chloride prepared according to the process of the present invention is stable and can be isolated.

After the reaction is completed a suitable solvent is added to the reaction mixture, and solvent is completely distilled off. The solvent is used for the removal of unreacted phosgene.

Scheme 1:

In an embodiment is provided a process for preparing and isolating the compound of formula (II) by reaction of 4-piperidinopiperidine with triphosgene in presence of suitable solvents and suitable base(s) as outlined in step (I) of the scheme. Proper monitoring of the reaction conditions and the The additional solvent is selected such that the distillation can be continued until the temperature rises to 65-70° C. After the complete distillation, the HCl salt obtained is subsequently treated with suitable base(s) in suitable solvent(s), preferably in situ, which yields the crystalline product, which was isolated by adding suitable antisolvent(s).

The suitable base used in step-I may be selected from suitable organic or inorganic bases. Suitable organic base is selected from C$_{(1-5)}$ alkyl amines, C$_{(1-5)}$ substituted alkyl amines such as triethyl amine (TEA), diisopropyl amine, diisopropylethyl amine, heterocyclic unsaturated amines like pyridine; suitable inorganic bases which can be used is selected from hydroxides such as NaOH, KOH and the like, carbonates such as NaHCO$_3$, Na$_2$CO$_3$, K$_2$CO$_3$ and the like, hydrides such as NaH, n-BuLi, LDA and KHMDS and the like or suitable mixtures of one or more from those described above.

The suitable solvent used in step-I may be selected from suitable hydrocarbons such as benzene, toluene, xylene, ethyl benzene, trimethyl benzene and the like; ethers such as tetrahydrofuran and the like, halogenated hydrocarbon solvents such as chloroform, dichloromethane, dichloroethane & the like; ketones such as acetone & the like; aprotic polar solvents such as dimethylformamide, dimethyl acetamide & the like or suitable mixtures of one or more from those described above.

The suitable anti-solvent used for crystallizing the free base (II) in step-I may be selected from suitable hydrocarbons such as C$_{(5-10)}$ alkane, C$_{(5-10)}$ cycloalkane, toluene & the like; ethers such as tetrahydrofuran & the like or suitable mixtures of one or more from those described above.

In one aspect the present invention provides a process for isolation of [1,4']bipiperidinyl-1'-carbonyl chloride intermediate compound of formula (II) free from its hydrochloride salt or its dimer impurity.

In a preferred embodiment, the [1,4']bipiperidinyl-1'-carbonyl chloride intermediate compound of formula (II) is obtained as a stable compound.

In a further embodiment of the invention is disclosed a crystalline form of the [1,4']bipiperidinyl-1'-carbonyl chloride, which has at least one of the following characteristics: i) a powder X-ray diffraction pattern substantially in accordance with FIG. 3;
ii) a powder X-ray diffraction pattern having peaks at about 6.27, 16.08, 17.15, 18.35, 22.23, 22.83 and 29.22±0.2 degrees 2θ;
iii) a powder X-ray diffraction pattern having additional peaks at about 11.10, 12.45, 14.07, 20.31, 25.18 and 27.38±0.2 degrees 2θ;

The crystalline form of [1,4']bipiperidinyl-1'-carbonyl chloride as above is further characterized by a DSC comprising onset peaks at about 208° C.±2° C. and endotherm peak about 212° C.±2° C.

The crystalline form of [1,4']bipiperidinyl-1'-carbonyl chloride is an intermediate and helps in obtaining the compound of formula (I) and also CPT-11 in a pure form and also this crystalline form helps in obtaining a clean reaction and clean final product i.e. compound of formula (I) as well as CPT-11.

In an embodiment is provided a process for preparing compound of formula (I) comprising, reacting [1,4']-bipiperidinyl-1'-carbonyl chloride (II) with 7-ethyl-10-hydroxy camptothecin (III) in the presence of suitable base(s), suitable amide(s), pyridine and using suitable solvent(s) as per step 11 of the scheme.

Suitable amide used in step-II may be selected from dimethylformamide, dimethyl acetamide and acetamide, most preferable being acetamide.

The suitable solvent(s) used in step-II may be selected from suitable hydrocarbons such as benzene, xylene, ethyl benzene, trimethyl benzene; halogenated hydrocarbon solvents such as chloroform, dichloromethane, dichloroethane and the like; aprotic solvents such as dimethylformamide, dimethyl acetamide or mixtures thereof.

The suitable base used in step-II may be selected from suitable amines and most preferably, triethyl amine (TEA).

The duration of the reaction may be from 1 h to 5 hrs, more specifically 2 to 3 hrs.

In an embodiment of the invention, compound of formula (I) is crystallized from a suitable crystallization solvent, which may be selected from suitable alcohols, nitriles, and hydrocarbons, most preferably hexane.

In a further embodiment of the invention is disclosed a crystalline form of the compound of formula (I), which has at least one of the following characteristics:

i) a powder X-ray diffraction pattern substantially in accordance with FIG. 2;

ii) a powder X-ray diffraction pattern having peaks at about 6.36, 7.28, 10.40, 12.02, and 20.93±0.2 degrees 2θ;

iii) a powder X-ray diffraction pattern having additional peaks at about 14.61, 15.83, 18.30, 24.17 and 26.43±0.2 degrees 2θ.

The crystalline form of compound of formula (I) as disclosed above having a characteristic XRD & DSC can also be converted to chemically and chirally pure CPT-11. Thus, the new crystalline form of the base is suitable for obtaining chemically and chirally pure to 7-ethyl-10-[4-(1-piperidino)-1-piperidino]carbonyloxy-camptothecin hydrochloride trihydrate according to the present invention in a one step process.

In an embodiment of the invention, compound of formula (I) is converted to 7-ethyl-10-[4-(1-piperidino)-1-piperidino]carbonyloxy-camptothecin hydrochloride trihydrate by reacting with hydrochloric acid in suitable solvent as per step (III).

The suitable solvent(s) used in step-III may be selected from water and mixture of water and alcohols. The resulting crystalline product has a purity as measured by high performance liquid chromatography (HPLC, area % of the main peak) of at least 99.9%, even 100%, without any additional purification steps like chromatographic purification etc. being required, which have been used in prior art processes.

In an embodiment of the invention, CPT-11 obtained above, is crystallized from suitable crystallization solvent(s) which may be selected from alcohols, nitriles, and hydrocarbons most preferably hexane.

In a further embodiment of the invention disclosed a crystalline form of the CPT-11 which has at least one of the following characteristics:

i) a powder X-ray diffraction pattern substantially in accordance with FIG. 1;

ii) a powder X-ray diffraction pattern having peaks at about 7.60, 8.21, 9.55, 10.96, 12.34, 14.33, 15.79, 19.92, 21.25, 22.73, 24.79, 25.99 and 27.68±0.2 degrees 2θ;

Surprisingly, the present inventors have found that by the process of preparation of the present invention as described in Scheme 2, a new impurity was being formed not known earlier.

The present invention thus provides a new impurity of CPT-11, Compound X and having chemical name (S)-4,11-diethyl-3,14-dioxo-3,4,12,14-tetrahydro-1H-pyrano[3',4':6,7]indolizino[1,2-b]quinoline-4,9-diyl bis([1,4'-bipiperidine]-1'-carboxylate), and which has the following chemical structure:

Formula X

The Compound X was characterized by the following data:

Compound X has the following ¹H NMR (400 MHz, DMSO-$d_6$) δ (ppm): (0.83, t, 3H), (0.90, t, 3H), (1.21, m, 2H), (1.27, t, 2H), (1.30-1.70, m, 20H of PP), (2.10-4.40, m, 18H of PP), (5.34, s, $CH_2$—N), (5.45, s, $CH_2$—O), (6.99, d, aromatic proton), (7.66, d, 1H, aromatic proton), (7.98, s, 1H, aromatic proton), (8.15, s, 1H, aromatic proton)

Mass analysis: MS data for Compound X is given below.

| Peak Report | | |
|---|---|---|
| Assignation | M Calculated (Da) | M measured (Da) |
| [M + H]⁺ | 780.95 | 781.5 |
| SN-38 as daughter ion | 391.4 | 391.3 |

In another aspect, the invention encompasses a process for synthesizing the compound of formula (X) as described in scheme 2, whereby the reaction of compound of formula (I) and compound of formula (II) in presence of suitable base and in a suitable solvents yield (S)-4,11-diethyl-3,14-dioxo-3,4,12,14-tetrahydro-1H-pyrano[3',4':6,7]indolizino[1,2-b]quinoline-4,9-diyl bis([1,4'-bipiperidine]-1'-carboxylate) of formula (X).

Scheme 2:

The suitable solvent(s) used for the formation of compound of formula (X) may be selected from halogenated solvent such as chloroform, dichloromethane, dichloroethane and like; nitriles such as acetonitrile; esters such as ethyl acetate and like; ethers like diethyl ether, 1,4-dioxane, dimethoxy ethane, DIPE, MTBE, THF and their suitable mixtures.

The suitable base used for the formation compound of formula (X) may be selected from pyridine, TEA, Morpholine, n-Methyl morpholine, Dimethyl amino pyridine and like.

In order to obtain marketing approval for a new drug product, manufacturers must submit to the regulatory authority evidence that the product is acceptable for administration to humans. Such a submission must include impurity profile of the product to demonstrate that the impurities are either absent, or present in a negligible amount. Different regulatory authorities have promulgated guidelines requiring applicants to identify the impurities present in the product and also disclose their concentration in the product. They also provide the maximum level of impurities allowable in the product. Thus for e.g. USFDA recommends that drug applicants identify all the impurities having concentration of 0.1% or greater in the active ingredient. Therefore, there is a need to check impurity profile and identify the impurities and also their concentration in the active ingredient.

The product mixture of a reaction rarely is a single compound pure enough to comply with pharmaceutical standards. Side products and byproducts of the reaction and adjunct reagents used in the reaction will, in most cases, be present. At certain stages during processing of the CPT-11 contained in the product mixture into an active pharmaceutical ingredient, it must be analyzed for purity, typically by HPLC or GC analysis.

Generally, impurities (side products, byproducts and adjunct reagents) are identified spectroscopically and by other physical methods and then the impurities are associated with a peak position in a chromatogram. Thereafter, the impurity can be identified by its position in the chromatogram, which is conventionally measured in minutes between injection of the sample on the column and elution of the particular component through the detector, known as "retention time". This time period varies daily based upon the condition of the instrumentation and many other factors. To mitigate the effect that such variations have upon accurate identification of an impurity, practitioners use "relative retention time" (RRT) to identify impurities. The RRT of an impurity is its retention time divided by the retention time of some reference marker. Thus, it is sometimes desirable to select an alternative compound that is added to, or is present in, the mixture in an amount significant enough to be detectable and sufficiently low as not to saturate the column and to use that as the reference marker. Researchers and developers in drug manufacturing understand that a compound in a relatively pure state can be used as a reference standard" (a "reference marker is similar to a reference standard but it is used for qualitative analysis) to quantify the amount of the compound in an unknown mixture. When the compound is used as an "external standard" a solution of a known concentration of the compound is analyzed by the same technique as the unknown mixture.

The reference standard compound also can be used to quantify the amount of another compound in mixture if the "response factor", which compensates for differences in the sensitivity of the detector to the two compounds, has been predetermined.

The reference standard compound can even be used as an internal standard when the unknown mixture contains some of the reference standard compound by using a technique called "standard addition" wherein at least two samples are prepared by adding known and differing amounts of the internal standard. The proportion of detector response due to the reference standard compound that is originally in the mixture can be determined by extrapolation of a plot of detector response versus the amount of the reference standard compound that was added to each of the sample to zero.

The compound of formula (X) may be used as an internal or external reference standard. The compound in a relatively pure state can be used as a reference standard" (a "reference marker is similar to a reference standard but it is used for qualitative analysis) to quantify the amount of the compound in an unknown mixture. When the compound is used as an "external standard" a solution of a known concentration of the compound is analyzed by the same technique as the unknown mixture.

The invention is further exemplified by the following non-limiting examples, which are illustrative representing the preferred modes of carrying out the invention. The invention's scope is not limited to these specific embodiments only but should be read in conjunction with what is disclosed anywhere else in the specification together with those information and knowledge which are within the general understanding of a person skilled in the art.

Example 1

[1,4']bipiperidinyl-1'-carbonyl chloride (II)

In a solution of Triphosgene (16.48 gm) in methylene chloride (200 ml) was added a solution of 4-piperidinopiperidine (20 g) in methylene chloride (200 ml) at 20-25° C. within 1-2 hours. Part of the methylene chloride was distilled off and acetonitrile was added. Further, methylene chloride and acetonitrile was distilled off completely until the temperature rises to 70° C. At room temperature fresh methylene chloride was added to the reaction mixture to make homogenous slurry followed by potassium carbonate (30-35 gm) and reaction mixture was stirred for 1-2 hours. The reaction mixture was filtered and subsequently the filtrate was concentrated. Hexane was added slowly into the reaction mixture under stirring. Solid compound so obtained was filtered, washed with hexane and dried under reduced pressure at about 40° C.

Yield—27 g (98.5%); GC purity: 99.80%; Dimeric Impurity: Not Detected

Example 2

7-ethyl-10-[4-(1-piperidino)-1-piperidino]carbonyloxy-camptothecin (I)

In a suitable vessel were charged 7-Ethyl-10-hydroxy-camptothecin (20 g), methylene dichloride, acetamide (3 gm) and pyridine (60 ml) under nitrogen atmosphere. A solution of [1,4']bipiperidinyl-1'-carbonyl chloride (17.6 g), methylene dichloride and triethylamine (20 ml) was prepared and added to the above suspension and stirred at 30-40° C. for 2 hours. The solvent was distilled out under reduced pressure at 50° C. and hexane was added under stirring as an antisolvent to isolate crystalline compound. The crystalline compound was filtered, washed with hexane and dried under reduced pressure at 50° C. The yield was 28.4 g (95%). HPLC Purity—99.9%

Example 3

7-ethyl-10-[4-(1-piperidino)-1-piperidino]carbonyloxy-camptothecin (I)

In a suitable vessel were charged 7-Ethyl-10-hydroxy-camptothecin (1 g), methylene dichloride, dimethylformamide (0.186 gm) and pyridine (3 ml) under nitrogen atmosphere. A solution of [1,4']bipiperidinyl-1'-carbonyl chloride (0.88 g), methylene dichloride and triethylamine (1 ml) was prepared and added to the above suspension and stirred at 30-40° C. for 2 hours. The solvent was distilled out under reduced pressure at 50° C. and hexane was added under stirring as an antisolvent to isolate crystalline compound, which was then filtered, washed with hexane and dried under reduced pressure at 50° C. The yield was 1.30 g (86.89%); HPLC purity—99.8%

Example 4

7-ethyl-10-[4-(1-piperidino)-1-piperidino]carbonyloxy-camptothecin (I)

In a suitable vessel were charged 7-Ethyl-10-hydroxy-camptothecin (1 g), methylene dichloride, dimethyl acetamide (0.221 gm) and pyridine (3 ml) under nitrogen atmosphere. A solution of [1,4']bipiperidinyl-1'-carbonyl chloride (0.88 g), methylene dichloride and triethylamine (1 ml) was prepared and added to the above suspension and stirred at 30-40° C. for 2 hours. The solvent was distilled out under reduced pressure at 50° C. and hexane was added under stirring as an antisolvent to isolate crystalline compound which was then filtered, washed with hexane and dried under reduced pressure at 50° C. The yield was 1.25 g (83.55%); HPLC purity-99.9%

Example 5

7-ethyl-10-[4-(1-piperidino)-1-piperidino]carbonyloxy-camptothecin hydrochloride Trihydrate (CPT-11)

In a suitable vessel were charged 7-ethyl-10-[4-(1-piperidino)-1-piperidino]carbonyloxy-camptothecin (27 gm) obtained in Example 2 and purified water. Subsequently, concentrated hydrochloric acid (5.76 gm) was added to dissolve the reaction mass completely. Reaction mass was treated with activated carbon and filtered. Further concentrated hydrochloric acid (13.5 gm) was added to the filtrate at 60-70° C. and the reaction mixture was maintained at 2-5° C. for 20 hours. The product so obtained was filtered, washed with isopropanol and dried under reduced pressure at 50° C. The yield was 28 g (90%); HPLC purity 100%.
i) a powder X-ray diffraction pattern substantially in accordance with FIG. 1;
ii) a powder X-ray diffraction pattern having peaks at about 7.60, 8.21, 9.55, 10.96, 12.34, 14.33, 15.79, 19.92, 21.25, 22.73, 24.79, 25.99 and 27.68±0.2 degrees 2θ;

Example 6

(S)-4,11-diethyl-3,14-dioxo-3,4,12,14-tetrahydro-1H-pyrano[3',4':6,7]indolizino[1,2-b]quinoline-4,9-diyl bis([1,4'-bipiperidine]-1'-carboxylate)

Compound of Formula-X

Charged 1 gm (1.7 mmol) of Irinotecan free base, 10 mL of MDC, 3 ml of pyridine and 150 mg of Acetamide in a flask. Prepared a solution of 0.56 gm (2.27 mmol) [1,4']bipiperidinyl-1'-carbonyl chloride (II) in 15 mL of MDC and 1 mL of TEA in another flask and added in above reaction mass. The temperature of reaction mass was raised to 30-35° C. and maintained for 48 hrs. The reaction mass was washed with 5 mL of 5% NaHCO$_3$ and evaporated in vacuum. To the reaction mass toluene was added and again evaporated completely. Added 10 mL of n-Hexane and stirred for 30 min, filtered and washed with n-Hexane to get the product which was purified by column chromatography by eluting with MDC:Methanol (95:5%) to afford 208 mg of title compound having 99% purity by HPLC. M.P.=227° C.

We claim:
1. A process for preparing 7-ethyl-10-[4-(1-piperidino)-1-pipericlino]carbonyloxy-camptothecin hydrochloride trihydrate comprising the steps of:
i) reacting 4-piperidinopiperidine with triphosgene in presence of dichloromethane and suitable base to obtain [1,4']bipiperidinyl-1'-carbonyl chloride of formula (II), ii) reacting [1, 4']bipiperidinyl-1'-carbonyl chloride (II) with 7-ethyl-10-hydroxy camptothecin (III) in the presence of (a) suitable amide, (b) pyridine and (c) a base other than pyridine in a suitable solvent to obtain compound of formula (I), and iii) converting 7-ethyl-10-[4-(1-piperidino)-1-piperidino] carbonyloxy-camptothecin into hydrochloride trihydrate (CPT-11) by reacting with hydrochloric acid in suitable solvent, wherein the suitable solvent is selected from water, alcohol(s), or a mixture of thereof 4. The process according to claim 1, wherein the solvent used in step ii) is selected from the group consisting of ethers, esters, hydrocarbons, halogenated hydrocarbons, dimethylformamide, DMSO, DMAc, NMP, and acetonitrile or a mixture thereof.

(I)

(CPT-11)

2. The process according to claim 1, wherein the base used in step i) is selected from the group consisting of alkyl amines, and inorganic bases selected from alkali metal hydroxides, alkali metal carbonates and alkali metal bicarbonates; or a mixture thereof.

3. The process according to claim 1, wherein the amide used in step ii) is selected from the group consisting of dimethylformamide, dimethyl acetamide, and acetamide or a mixture thereof.

5. The process according to claim 1 wherein the base used in step ii) is selected from amines.

6. The process according to claim 1, wherein the solvent used in step iii) is water.

7. The process according to claim 5, wherein the base is triethylamine.

8. The process according to claim 1, wherein the solvent used in step iii) is alcohol(s).

* * * * *